United States Patent

Donges et al.

[11] Patent Number: 4,736,401
[45] Date of Patent: Apr. 5, 1988

[54] X-RAY SCANNER

[75] Inventors: Gerhard Donges, Heidenrod-Kemel; Thomas Herwig, Eltville; Cornelius Koch; Georg Geus, both of Wiesbaden, all of Fed. Rep. of Germany

[73] Assignee: Heimann GmbH, Fed. Rep. of Germany

[21] Appl. No.: 843,377

[22] Filed: Mar. 24, 1986

[30] Foreign Application Priority Data

Apr. 3, 1985 [DE] Fed. Rep. of Germany ....... 3512228

[51] Int. Cl.$^4$ .......... H05G 1/64; G21K 5/10; G01B 15/00
[52] U.S. Cl. ...................... 378/146; 378/58; 378/99
[58] Field of Search ............. 378/146, 99, 69, 137, 378/58, 12, 113; 250/359.1

[56] References Cited

U.S. PATENT DOCUMENTS 4,352,986  2/1982  Pfeiler ........................... 378/146
4,366,382  12/1982 Kotowski .
4,383,327  5/1983  Kruger ........................... 378/143

FOREIGN PATENT DOCUMENTS 0011338  8/1979  European Pat. Off. .
56149246  5/1983  Japan .

OTHER PUBLICATIONS

"Automated X-Ray Bomb Detection Techniques," Bisignani et al., 8079 Electro Conf., Record vol. 4, (1979-04-24/26).
Heimann Brochure, "Komponenten Der Pruftechnik".

Primary Examiner—Carolyn E. Fields
Assistant Examiner—Joseph A. Hynds
Attorney, Agent, or Firm—Hill, Van Santen, Steadman & Simpson

[57] ABSTRACT

An X-ray scanner for examining objects moved through an X-ray beam on a conveyor has a detector array disposed at the opposite side of the conveyor from the X-ray source and a pulse generator connected to the motor which drives the conveyor for generating a pulse trail dependent on the speed of the motor, and hence on the speed of the conveyor. The pulse generator is connected to a scanner for the detector array and controls the scan rate dependent upon the conveyor speed. The conveyor speed is controlled such that the quotient of the scan rate and the conveying speed is maintained constant in order to hold the imaging scale constant.

2 Claims, 1 Drawing Sheet

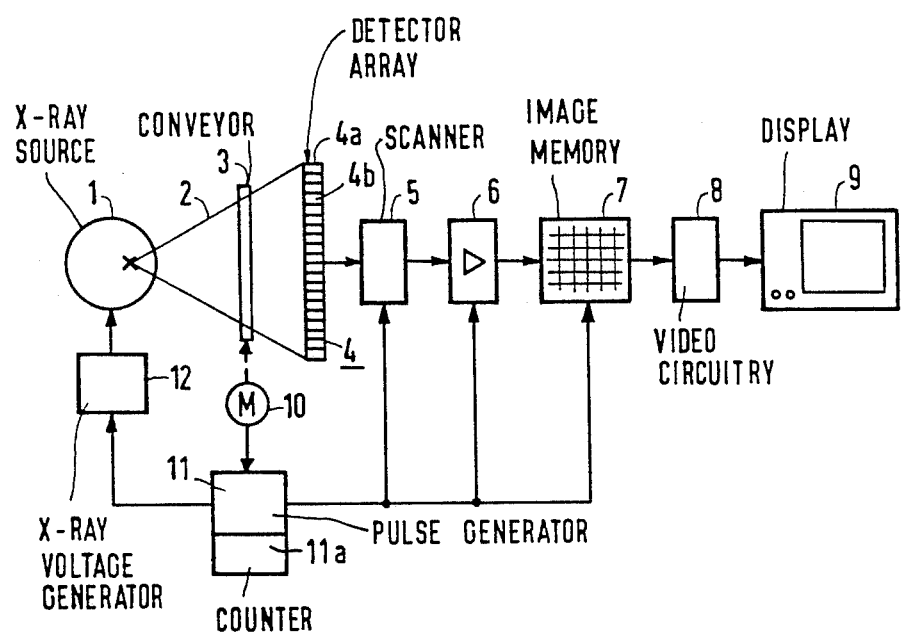

X-RAY SCANNER

BACKGROUND OF THE INVENTION

1. Field of the Invention

The present invention relates to x-ray scanning devices, and in particular to such devices having an x-ray source disposed on one side of a conveyor for generating a fan-shaped x-ray beam at objects on the conveyor and having a detector array on the opposite side of the conveyor for receiving the radiation passing through the conveyor and the objects thereon.

2. Description of the Prior Art

X-ray scanning devices for examining objects moving through an x-ray beam on a conveyor or other type of transport device having electronic circuitry for acquiring and processing signals received by a detector array and displaying the resulting image on a display unit are known in the art. Generally, the processing circuitry includes an image storage memory which employs one memory cell for each detector within the array, and also includes a scanning device for the detector array which supplies detector signals to the image storage memory.

X-ray examination devices of this type are used, for example, for examining baggage. The objects to be examined are moved past the detector array, generally in the form of a detector line or row, which is disposed in a plane perpendicular to the direction of conveyance of the objects. The objects are moved on the conveyor with a specific speed.

Because of the line or row structure of the detector array, the material or objects to be examined are scanned in strips. After converting to a digital signal, the samples, the number of which depends upon the number of detectors, are either evaluated in real time or are entered into a memory in order to construct a video image.

The imaging scale M on the display unit, as viewed in the running or conveying direction, is a function of the scan rate A and of the running speed V of the object or material to be examined, and can be calculated according to the following relationship:

$$M = A/V \times K$$

In the above equation, K is a system constant which, for example, accounts for image format and pixel size.

In practice, the requirement that the conveying device have variable speed is often necessary in order to enable optimum matching to the examination or production sequence in which the device is being used. This can be done in combination with an x-ray scanning device only when changes in the scale in the running direction were accepted as well.

SUMMARY OF THE INVENTION

It is an object of the present invention to provide an x-ray scanning device for use with a conveyor wherein the imaging scale is maintained constant regardless of the conveying speed.

The above object is inventively achieved in an x-ray scanning device having a generator connected to the conveyor motor for generating a pulse train signal dependent upon the speed of the motor, and hence upon the speed of the conveyor. The generator is connected to the scanner for the detector array and controls the scan rate of the scanner such that the quotient of the scan rate and the conveying speed remains substantially constant. The scan rate for the detector line is controlled such that the imaging scale remains constant.

In a further embodiment of the invention, the processing circuitry includes a programmable amplifier which is controllable by the pulse generator so as to be dependent on the scan rate for the detector row and to maintain the output signal constant independently of the scan rate. Detectors generally integrate the incident radiation in a time interval which is proportional to the reciprocal of the scan rate, which is taken into account by controlling the amplifier. With increasing scan rate, the amplification is increased so that the signal amplitude can be maintained constant. In a further embodiment of the invention, the x-ray voltage generator connected to the x-ray source is also connected to and controlled by the pulse generator so that the x-ray source can be shut off when the conveyor device is at a standstill. Such measures avoid unacceptably high radiation doses directed at the material or objects to be examined when the conveyor device is stationary.

DESCRIPTION OF THE DRAWINGS

The single FIGURE is a schematic block diagram of an x-ray scanning device constructed in accordance with the principles of the present invention.

DESCRIPTION OF THE PREFERRED EMBODIMENTS

An x-ray scanning device constructed in accordance with the principles of the present invention is schematically shown in the drawing. The device includes an x-ray source 1 which emits a fan-shaped x-ray beam 2 in a plane disposed in the plane of the drawing. The x-ray beam 2 irradiates material or objects on a conveyor 3, the conveying direction of the conveyor 3 being perpendicular to the plane of the drawing. The x-radiation emerging from the material or objects on the conveyor 3 is received by a line or row array 4 of individual detectors 4a, 4b, etc. Each individual detector may consist, for example, of a scintillation crystal and a photodiode optically coupled thereto. The detector signals are successively read by a scanner 5 and are entered into an image storage memory 7 through a controllable amplifier 6. Entry of the data is undertaken such that one line in the image storage memory 7 is allocated to each detector 4a, 4b, etc. The image stored in the image storage memory 7 after a selected path has been traversed is reproduced on a display unit 9 through conventional video circuitry 8.

The conveyor 3 is driven by an electric motor 10 to which a pulse generator 11 for generating a pulse signal train dependent on the speed of the conveyor 3 is connected. The generator 11 is connected to the scanner 5 and controls the scan rate of the scanner 5 such that the quotient of the scan rate and the conveying speed remains constant. This ensures that the imaging scale on the visual display 9 also remains constant. The generator 11 may be, for example, an incremental generator. The clock or address generation for the line scan is acquired in this embodiment from a divider chain which includes programmable counters. A slight error arises due to the division ratio of the counter chain which is always whole-numbered. Both intentional and unintentional changes in the speed of the conveyor 3 are compensated by undertaking a modification of the scan rate in the opposite direction.

Conventional detectors integrate the incident radiation in a time interval which is proportional to the reciprocal of the scan rate. The output signal of such conventional detectors is therefore inversely proportional to the scan rate. The dependency of the signal amplitude on the scan rate is maintained constant by the programmable amplifier 6, connected to the pulse generator 11 and controlled thereby.

Continuous radiation in x-ray scanners is locally limited to the area surrounding the material or object under examination when the conveyor 3 is at a standstill. This results in an unacceptable high radiation dose for that material or object. In order to avoid such excessively high dosages, a conveyor standstill is detected by evaluating the output signal of the generator 11 in suitable evaluation circuitry contained therein, and the x-ray voltage generator 12, also connected to the generator 11, is shut off when such a standstill is detected, thereby also shutting off the x-ray source 1.

When the conveyor 3 is shut off, the conveyor will nonetheless move a certain distance after power is disengaged. Limits can be placed on the control of the scan rate in a known manner so that such unwanted movement of the conveyor is not misinterrupted as an actual operating condition. Additionally, the x-ray source 1 must be shut off shortly before a complete standstill of the conveyor 3, so that information may be lost if special measures are not undertaken. If such special measures are not undertaken, a continuous image is not possible.

In order to avoid these disadvantages, entry of the data in the image storage memory 7 is interrupted when the conveyor 3 is shut off and a counter 11a connected to the pulse generator 11 counts the number of pulses generated by the generator 11 to the point of standstill. Before re-energization of the conveyor 3, the conveyor 3 is driven in reverse until it is beyond the point at which shut off occurred. The incremental generator pulses are then subtracted from the counter reading, i.e., the counter 11a counts in reverse. When the conveyor 3 is re-started, the counter reading is, thus, initially negative. Entry of data into the image storage memory 7 is not resumed until the counter reading reaches zero, so that a continuous image is achieved.

The counter 11a or the generator 11 may be provided with logic circuitry of the type well known to those skilled in the art which begins the appropriate counting operation if the speed of the motor 10, and, thus, of the conveyor 3, is determined to be below a predetermined speed. The point in time at which the speed falls below this predetermined level may be then used as the point at which shut-off of the conveyor and/or the motor occurred. It is, of course, also possible to hard-wire a connection to a shut-off switch from the counter or the generator so as to provide a definite signal upon shut-off.

Although modifications and changes may be suggested by those skilled in the art it is the intention of the inventors to embody within the patent warranted hereon all changes and modifications as reasonably and properly come within the scope of their contribution to the art.

We claim as our invention:

1. An x-ray device for examining objects on a conveyor having a drive motor and for representing said objects on a visual display, said device comprising:
   means for generating a fan-shaped x-ray beam through which said objects move on said conveyor perpendicular to said beam, said means for generating including an x-ray voltage generator;
   a detector array for receiving radiation passing through said objects;
   means for scanning said array for acquiring data therefrom at a scan rate;
   a memory means for storing said data from said means for scanning for construction a video image for said visual display;
   a pulse generator means connected to said motor for generating a signal dependent on the speed of said conveyor and connected to said means for scanning for controlling said scan rate such that a ratio of the scan rate and the conveyor speed is maintained constant, and connected to said x-ray voltage generator for deenergizing said voltage generator is said signal indicates a conveyor standstill, and connected to said memory for interrupting entry of data therein if said conveyor is shut off, said conveyor being driven by said motor in reverse from the point of standstill for a selected distance following a shut down of said conveyor; and
   a counter means connected to said pulse generator means for counting pulses from the time said conveyor is shut off until said conveyor reaches a standstill, said counter means counting in reverse during the reverse drive of said conveyor and subtracting the reverse count from the forward count to insure said conveyor is reverse driven to a point beyond the point at which shut down occurred, and said counter means resuming a forward count upon restarting of said conveyor and enabling said pulse generator means to resume entry of data into said memory means only when the point at which shut down occured is again reached.

2. An x-ray device as claimed is claim 1, further comprising:
   a controllable amplifier connected between said means for scanning and said memory means, and to said pulse generator means, said pulse generator means controlling said amplifier dependent on said scan rate for maintaining the output of said amplifier at a level independent of changes in said scan rate.

* * * * *